United States Patent
Flowers et al.

(10) Patent No.: US 11,786,361 B2
(45) Date of Patent: Oct. 17, 2023

(54) HAPTIC OPTIC MANAGEMENT SYSTEM UTILIZING A SQUID CLIP

(71) Applicant: Alcon Inc., Fribourg (CH)

(72) Inventors: Matthew Braden Flowers, Aliso Viejo, CA (US); Andrew Thomas Schieber, Tustin, CA (US); Sudarshan B. Singh, Euless, TX (US); Marcus Antonio Souza, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 812 days.

(21) Appl. No.: 16/705,290

(22) Filed: Dec. 6, 2019

(65) Prior Publication Data

US 2020/0179101 A1    Jun. 11, 2020

Related U.S. Application Data

(60) Provisional application No. 62/777,801, filed on Dec. 11, 2018.

(51) Int. Cl.
*A61F 2/16* (2006.01)

(52) U.S. Cl.
CPC .............. *A61F 2/16* (2013.01); *A61F 2/1662* (2013.01); *A61F 2002/1682* (2015.04); *A61F 2002/1689* (2013.01); *A61F 2210/0014* (2013.01)

(58) Field of Classification Search
CPC .. A61F 2/16; A61F 2/1662; A61F 2002/1682; A61F 2002/1689; A61F 2210/0014; A61F 9/00754; A61F 2/167
USPC ......................................................... 606/107
See application file for complete search history.

(56) References Cited

U.S. PATENT DOCUMENTS

| | | | | |
|---|---|---|---|---|
| 6,605,093 | B1 * | 8/2003 | Blake .................... | A61F 2/1664 606/107 |
| 8,403,941 | B2 * | 3/2013 | Peterson ............... | A61F 2/1691 606/107 |
| 9,149,619 | B2 * | 10/2015 | Isaacs ............... | A61M 37/0069 |
| 10,154,898 | B2 * | 12/2018 | Raquin ................. | A61F 2/1678 |
| 2002/0022881 | A1 * | 2/2002 | Figueroa ................. | A61F 2/167 606/107 |
| 2003/0195522 | A1 * | 10/2003 | McNicholas ......... | A61F 2/1678 606/107 |
| 2004/0243141 | A1 * | 12/2004 | Brown .................. | A61F 2/1678 606/107 |

(Continued)

FOREIGN PATENT DOCUMENTS

| | | |
|---|---|---|
| CN | 103037806 A | 4/2013 |
| CN | 105792783 A | 7/2016 |

(Continued)

*Primary Examiner* — Kathleen S Holwerda
*Assistant Examiner* — Serenity A Miller
(74) *Attorney, Agent, or Firm* — PATTERSON + SHERIDAN, LLP

(57) ABSTRACT

Systems, methods, and devices for inserting an intraocular lens (IOL) assembly into an eye may be provided. In an exemplary aspect, the present disclosure is directed to a haptic optic management system. The haptic optic management system may include a housing. The haptic optic management system may further include a plate, wherein the plate is disposed within the housing. The haptic optic management system may further include a clip that engages the plate in the housing, wherein the clip comprises a clip body and a plurality of legs that extend from the clip body.

20 Claims, 12 Drawing Sheets

(56) References Cited

U.S. PATENT DOCUMENTS

| | | | |
|---|---|---|---|
| 2011/0046634 A1* | 2/2011 | Rathert | A61F 2/1678 606/107 |
| 2013/0304078 A1* | 11/2013 | Issacs | A61F 2/167 606/107 |
| 2016/0256316 A1 | 9/2016 | Van Noy et al. | |
| 2021/0186683 A1* | 6/2021 | Hangya | A61F 2/1678 |

FOREIGN PATENT DOCUMENTS

| | | |
|---|---|---|
| EP | 2074962 A1 | 7/2009 |
| EP | 2368526 A1 | 9/2011 |
| WO | 2010/031196 A1 | 3/2010 |
| WO | 2010105678 A1 | 9/2010 |
| WO | 2012/006616 A2 | 1/2012 |

* cited by examiner

HAPTIC OPTIC MANAGEMENT SYSTEM UTILIZING A SQUID CLIP

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded natural lens with an intraocular lens ("IOL"). A large incision site may cause a longer post-operation healing time. To reduce this healing time, typical operating procedures have shifted to making incisions of about 2 millimeters in size into the eye. While this smaller size of incision may reduce post-operation healing time, problems such as the size and functionality of the insertion tool may arise as the incision size continues to shrink. Typically, the insertion tool may be pre-loaded with the IOL that may be inserted into the patient's eye once the clouded natural lens is removed. The insertion tool may include a plunger for forcing the IOL out of the nozzle of the insertion tool. The plunger may have additional functions including haptic tucking and folding of the IOL. Once an incision has been made, the insertion tool may be inserted into the eye through the incision, and the folded IOL may be dispensed into the eye by actuation of the plunger. As the incision site decreases, the size of the nozzle of the insertion tool may decrease accordingly.

SUMMARY

In an exemplary aspect, the present disclosure is directed to a haptic optic management system. The haptic optic management system may include a housing. The haptic optic management system may further include a plate, wherein the plate is disposed within the housing. The haptic optic management system may further include a clip that engages the plate in the housing, wherein the clip comprises a clip body and a plurality of legs that extend from the clip body.

In another exemplary aspect, the present disclosure is directed to an insertion tool. The insertion tool may include a drive system that includes a body. The insertion tool may further include a plunger disposed in the drive system. The insertion tool may further include a nozzle. The insertion tool may further include a haptic optic management system positioned between the nozzle and the drive system for receiving a distal tip of the plunger. The haptic optic management system may include a housing. The haptic optic management system may further include a plate disposed in the housing. The haptic optic management system may further include a clip that engages the plate in the housing, wherein the clip comprises a clip body and a plurality of legs that extend from the clip body.

In another exemplary aspect, the present disclosure is directed to a method of delivering an intraocular lens. The method may include applying an external force upon a clip to compress the clip in a housing, wherein the housing contains the intraocular lens. The intraocular lens may include an optic and haptics that extend from a periphery of the optic. The method may further include engaging the haptics with the clip as the clip is compressed to cause the haptics to fold onto the intraocular lens. The method may further include moving the clip away from the intraocular lens to release a force applied to a plate holding the intraocular lens to cause the plate and the intraocular lens to roll. The method may further include actuating a drive system to dispense the intraocular lens through a nozzle and into an eye.

The different aspects may include one or more of the following features. The housing may include a through bore traversing a length of the housing from a first end of the housing to a second end of the housing. The plate may be disposed in the through bore. The plate may be elastic, herein the clip engages the plate to prevent the plate from returning to an original position. The plate may include a material selected from the group consisting of spring steel, nitinol, polyimide, silicone, coated metals, and combinations thereof. The haptic optic management system may include an intraocular lens disposed on a lens surface of the plate, wherein the intraocular lens may include an optic and haptics that extend from a periphery of the optic. The housing may include openings in a side the housing, wherein the openings comprise a central slit and a pair of slits, wherein the central slit is disposed between the pair of slits, wherein the clip extends through the openings into a through bore in the housing. The plurality of legs may include outer support legs that extend through the pair of slits in the housing to hold the plate in position and inner legs that extend through central slit. The clip body may include a spring portion and opposing gripping portions that extend from the spring portion. The clip may further include a center post that extends from the clip body, wherein the center post aligns the clip within the pair of slits of the housing. The plunger may be operable to engage an intraocular lens disposable in the haptic optic management system when the drive system is actuated to dispense the intraocular lens from the nozzle. The drive system may include a lever and a pneumatic system. The clip may include a plurality of legs that extend from the clip body. The plurality of legs may extend into the housing of the haptic optic management system. The applying the external force may cause at least a portion of the legs to compress closer together. The plurality of legs may include inner legs. The inner legs may engage the haptics to cause the haptics to fold over on top of the intraocular lens. The plurality of legs may include outer support legs, wherein moving the clip away from the intraocular lens causes feet of the outer support legs to release from engagement with the plate such that the plate rolls upon itself. The actuating the drive system may cause a plunger to displace the intraocular lens out of the housing through the nozzle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
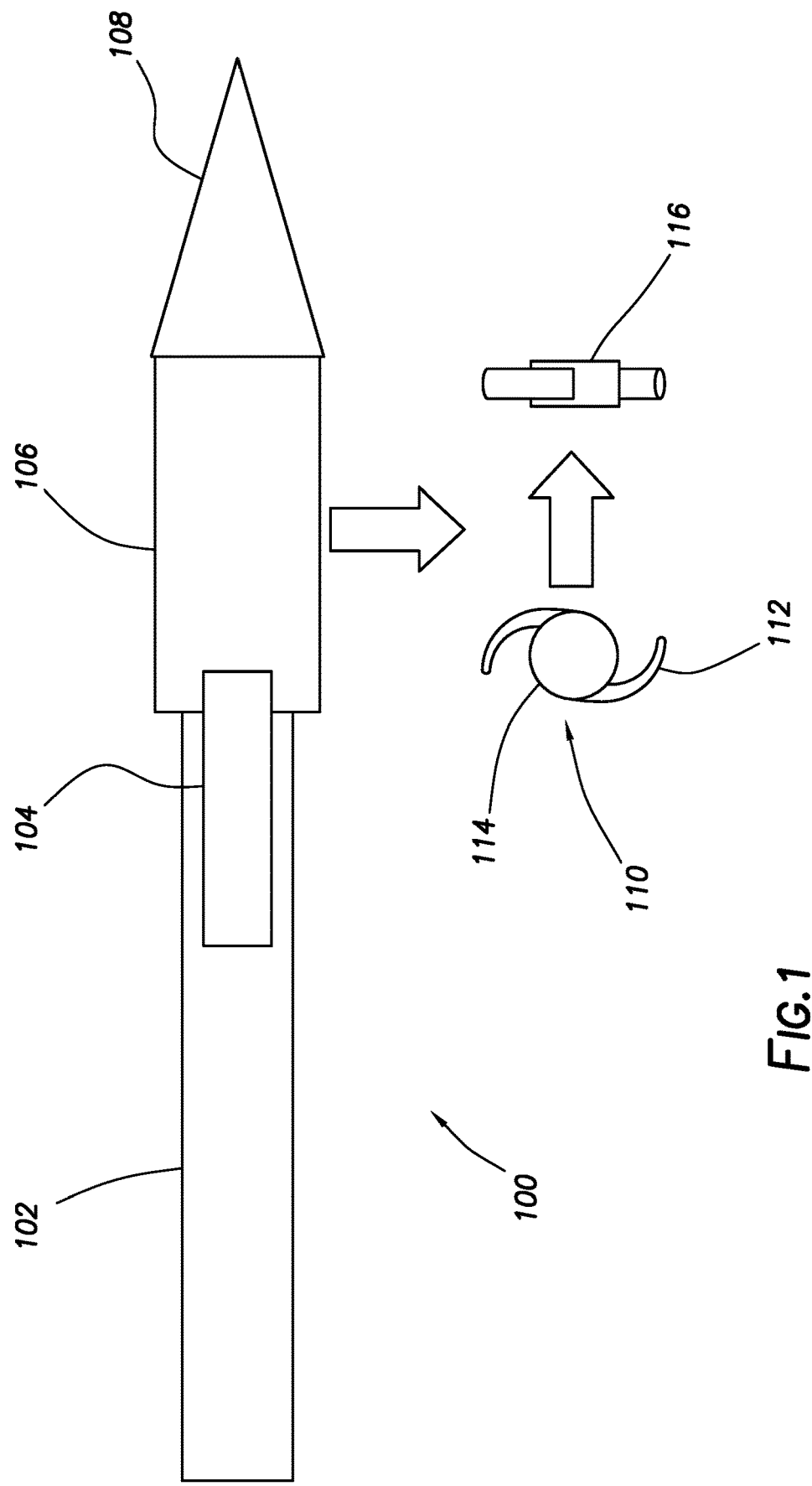
FIG. 1 illustrates a schematic of an example insertion tool operable to deliver an IOL into an eye.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers may be used throughout the drawings to refer to the same or like parts.

The example embodiments described herein generally relate to eye surgery. More particularly, the example embodiments generally relate to systems, methods, and devices for inserting an intraocular lens ("IOL") into an eye. Embodiments may include an insertion tool for preparation and delivery of the IOL into a patient's eye that includes a plunger, a nozzle, and a haptic optic management system. In some embodiments, the haptic management system may fold the IOL and tuck one or more haptics of the IOL. The haptic extends from an optic of the IOL and stabilizes the IOL when disposed within the capsular bag of the eye. After preparation of the IOL, the plunger forces the IOL through the insertion tool and out the nozzle.

FIG. 1 illustrates a schematic of an insertion tool 100. In some embodiments, insertion tool 100 may include a drive system 102, a plunger 104, a haptic optic management system (interchangeably referred to as "HOMS") 106, and a nozzle 108. The drive system 102 may be any system or combination of components operable to actuate the plunger 104. For example, the drive system 102 may utilize a lever and/or pneumatic systems; a manually driven system or component; an electromechanical system; a hydraulic system; or other device operable to drive the plunger 104 to advance; partially advance; or fully deliver an IOL 110 from the insertion tool 100. The plunger 104 is coupled to the drive system 102. The drive system 102 is operable to actuate the plunger 104. For example, the drive system 102 may be powered by, for example, electrically, mechanically, hydraulically, pneumatically, combinations thereof, or in some other manner. In response to the drive system 102, the plunger 104 moves through the HOMS 106. The HOMS 106 may be located between the drive system 102 and the nozzle 108. In alternate embodiments, the HOMS 106 may be disposed at other locations within the insertion tool 100. In some embodiments, the HOMS 106 may contain an IOL 110 in an unfolded position.

The drive system 102 may be any system, component, or group of components operable to advance an IOL 110 through the insertion tool 100. For example, the drive system 102 include plunger, schematically shown as plunger 104 in FIG. 1, that is operable to engage the IOL 110 disposed within the insertion tool 100 and advance the IOL 110 within the insertion tool 100. In some instances, the plunger 104 is operable to expel the IOL from the insertion tool 100.

In some instances, the drive system 102 may be a manually driven system. That is, in some instances, a user applies a force to cause the drive system 102 to operate. An example drive system 102 includes a plunger 104 that is manually engageable directly or indirectly by a user to push the plunger 104 through the insertion tool 100. When advanced, the plunger 104 engages an IOL 110 and advances the IOL 110 through the insertion tool 100, which may also include expelling the IOL 110 from the insertion tool 100. A non-limiting example of a manual IOL insertion tool is shown in U.S. Patent Application Publication No. 2016/0256316, the entire contents of which are incorporated herein by reference in its entirety. According to other implementations, the drive system 102 may be an automated system. Example automated drive systems are shown in U.S. Pat. Nos. 8,808,308; 8,308,736; and 8,480,555, the entire contents of each being incorporated herein by reference in their entirety. Still further, other automated drive systems within the scope of the present disclosure are described in U.S. Pat. No. 8,998,983 and U.S. Patent Application Publication No. 2017/0119522, the entire contents of each being incorporated herein by reference in its entirety. While example drive systems are provided as examples, these systems are not intended to be limiting. Rather, any component, group of components, systems, devices, mechanisms, or combinations thereof operable to advance an IOL 110 is within the scope of the present disclosure.

As shown in FIG. 1, the IOL 110 is a single piece IOL that includes an optic 114 and haptics 112 extending from opposing sides of the optic 114. For example, in the example IOL 110 shown in FIG. 1, the haptics 112 are disposed 180° relative to each other along an outer periphery of the optic 114. However, other types of IOLs are within the scope of the disclosure. For example, a multi-piece IOL, in which the optic and one or more haptics are separate components, may also be used.

Figure 2A:
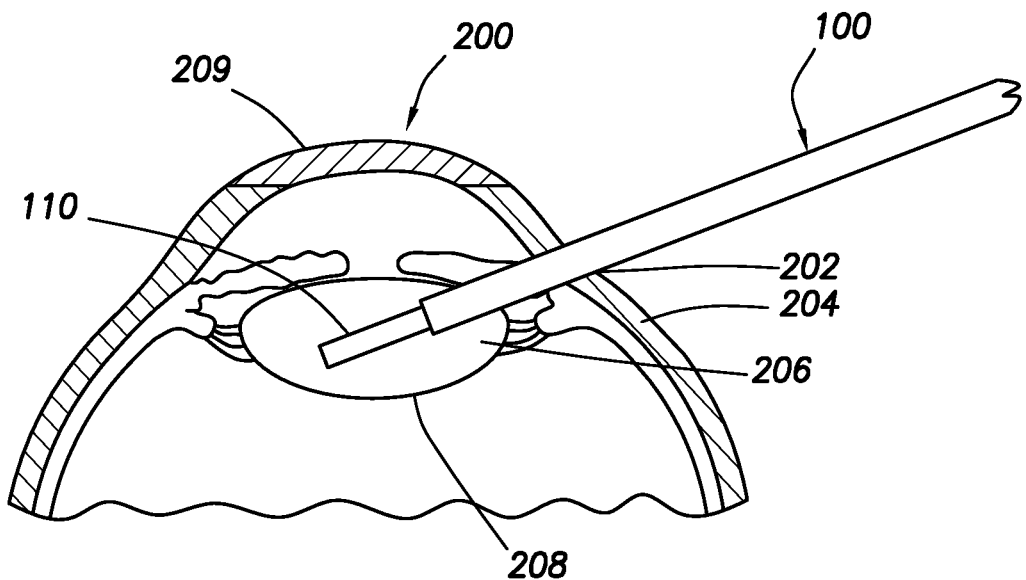
FIG. 2A illustrates an eye in which an IOL is being introduced from an insertion tool.

The IOL 110 may have a shape similar to that of a natural lens of an eye (e.g., eye 200 shown in FIG. 2A). The IOL 110 may be made from a numerous materials including, but not limited to, silicone, acrylic, and/or combinations thereof. Other materials are also contemplated. The haptics 112 extend from a periphery of the optic 114 and function to stabilize the IOL 110 when disposed within an eye.

In some instances, the HOMS 106 may be actuated to tuck the haptics 112 over the optic 114 and fold the optic 114. For example, the HOMS 106 may operate to fold the haptics 112 over the optic 114 and fold the optic 114 over or around the folded haptics 112. The IOL 110 is shown in a folded configuration at 116. The folded configuration 116 of the optic 114 may involve one or more haptics 112 folded relative to the optic 114 and, in some instances, the optic 114 folded relative to one or more of the haptics 112. The plunger 104 may be advanced through the HOMS 106 once the HOMS 106 has folded the IOL 110. As the plunger 104 moves through the HOMS 106, the plunger 104 displaces the folded IOL 110 from the HOMS 106. For example, the plunger 104 may force the folded IOL 110 into and through the nozzle 108.

FIG. 2A illustrates an eye 200 of a patient undergoing an operation with insertion tool 100. As illustrated, the insertion tool 100 dispenses a folded IOL 110 into the eye 200 of a patient. In some embodiments, an incision 202 is made in the eye 200 by a surgeon, for example. For example, in some instances, the incision 202 may be made through the sclera 204 of the eye 200. In other instances, an incision may be formed in the cornea 209 of the eye 200. The incision 202 may be sized to permit insertion of a portion of the insertion tool 100 in order to deliver the folded IOL 110 into the capsular bag 208. For example, in some instances, the size of the incision 202 may have a length less than about 2000 microns (2 millimeters). In other instances, the incision 202 may have a length of from about 0 microns to about 500 microns, from about 500 microns to about 1000 microns, from about 1000 microns to about 1500 microns, or from about 1500 microns to about 2000 microns.

After the incision 202 is made, the insertion tool 100 is inserted through the incision into an interior portion 206 of the eye 200. The insertion tool 100 is actuated to dispense the folded IOL 110 into the capsular bag 208 of the eye 200. Upon dispensation, the folded IOL 110 reverts to an initial, unfolded state, and the IOL 110 settles within the capsular bag 208 of the eye 200, as shown on FIG. 2B. The capsular bag 208 holds the IOL 110 within the eye 200 in a relationship relative to the eye 200 so that the optic 114 refracts light directed to the retina (not shown). The haptics 112 of the IOL 110 engage the capsular bag 208 to secure the IOL 110 therein. After dispensing the IOL 110 into the capsular bag 208, the insertion tool 100 is removed from the eye 200 through the incision 202, and the eye 200 is allowed to heal over a period of time.

Figure 2B:
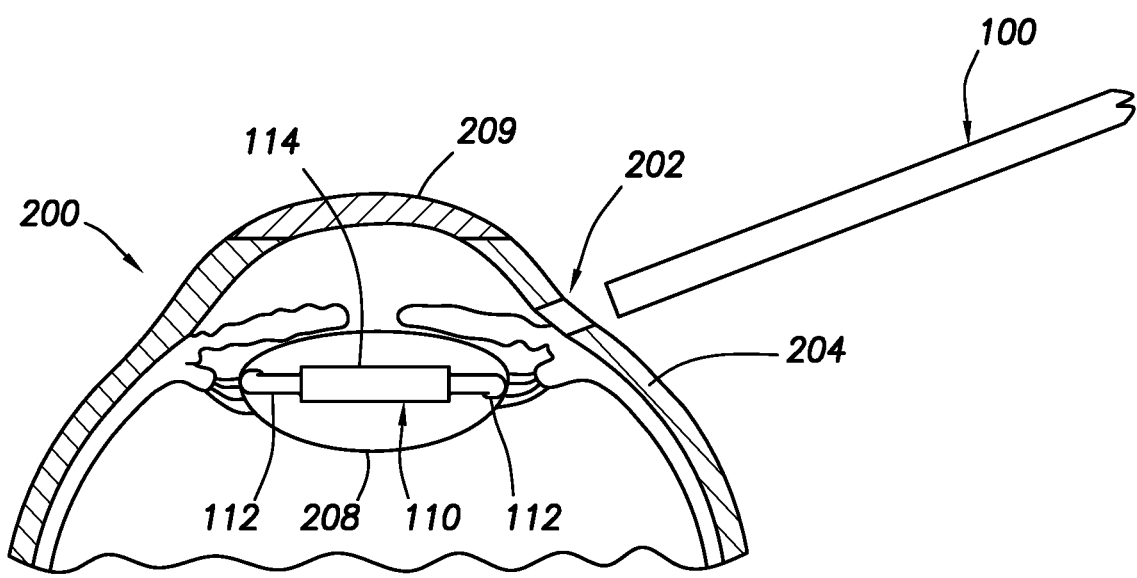
FIG. 2B illustrates the eye shown in FIG. 2A in which the IOL is positioned within the capsular bag of the eye and the insertion tool removed from the eye.
Figure 3:
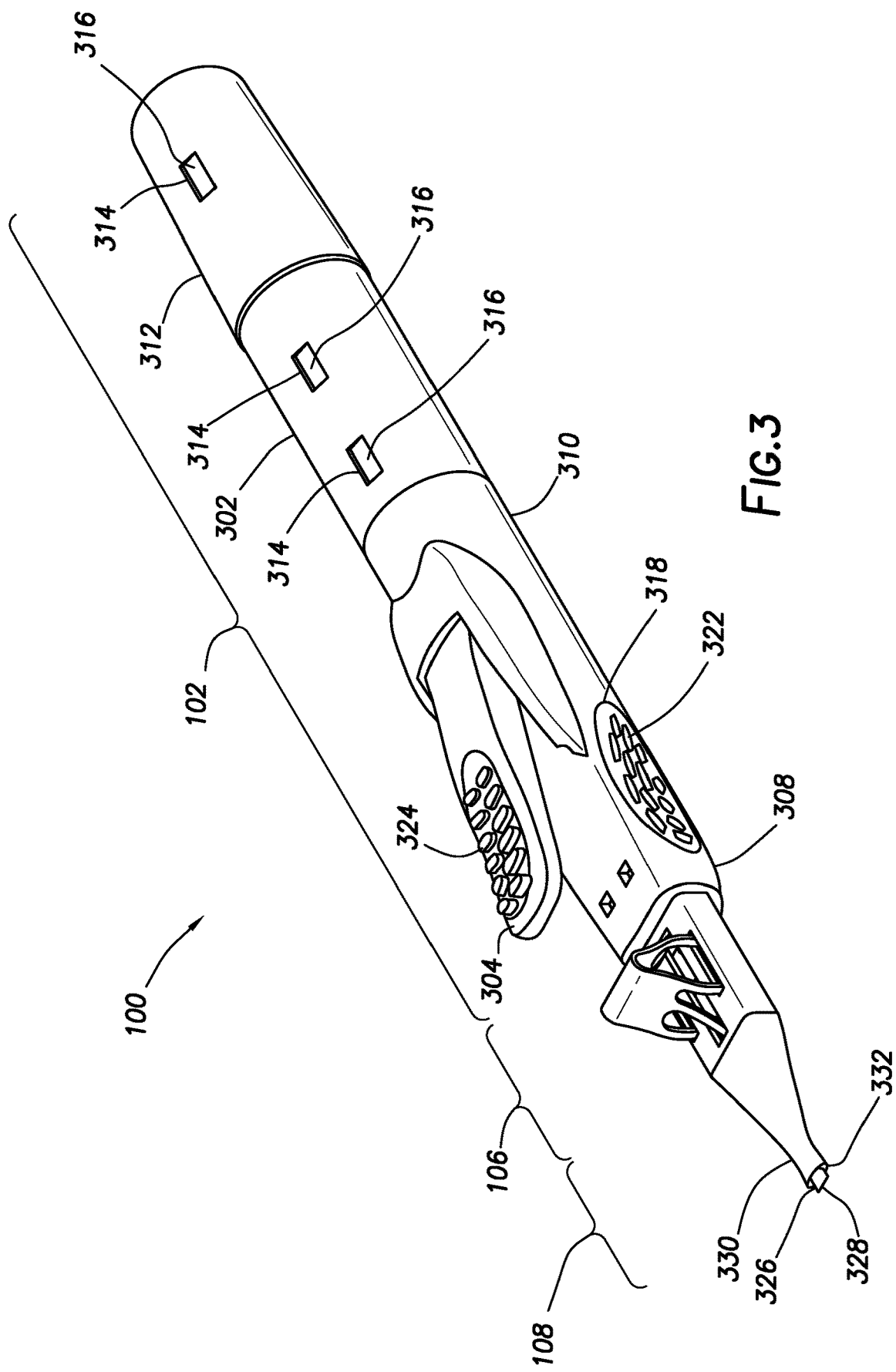
FIG. 3 illustrates a perspective view of another example insertion tool operable to delivery an IOL into an eye.
Figure 4:
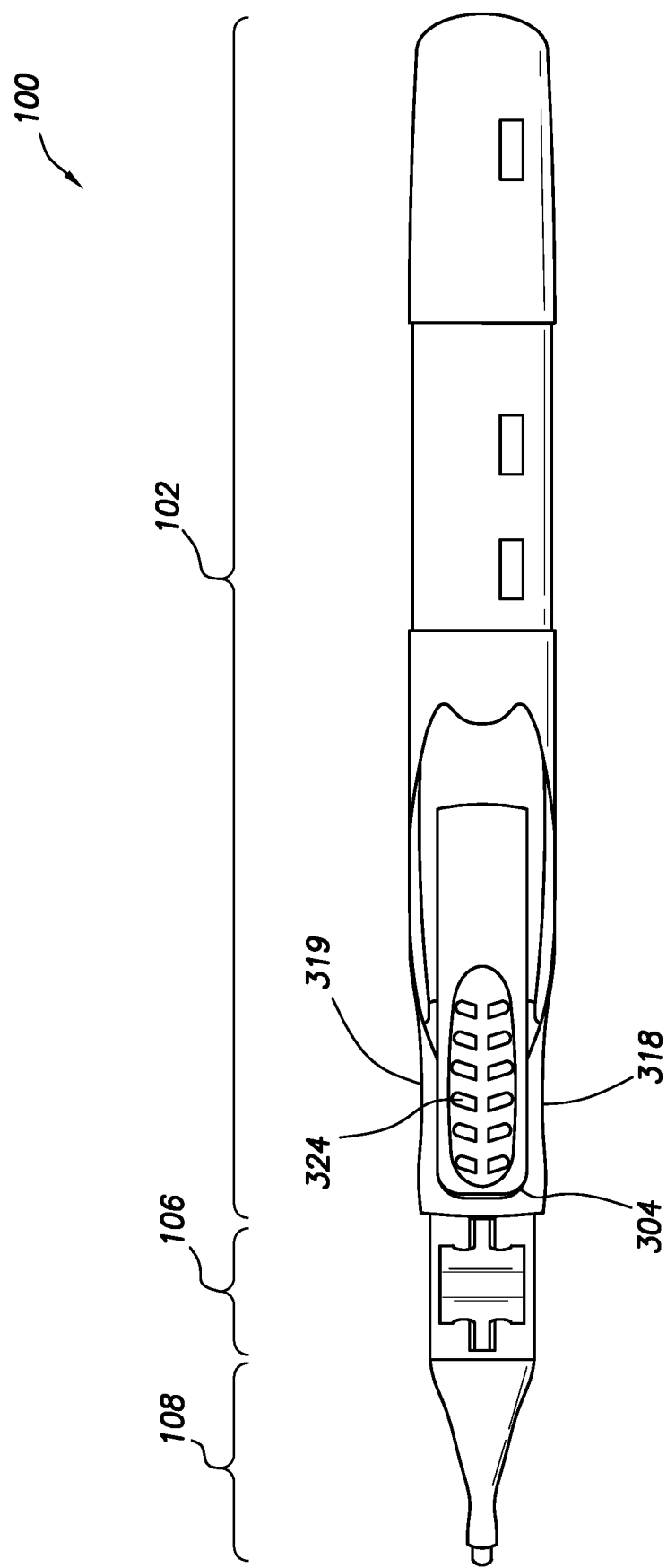
FIG. 4 illustrates a top view of the insertion tool of FIG. 3.
Figure 5:
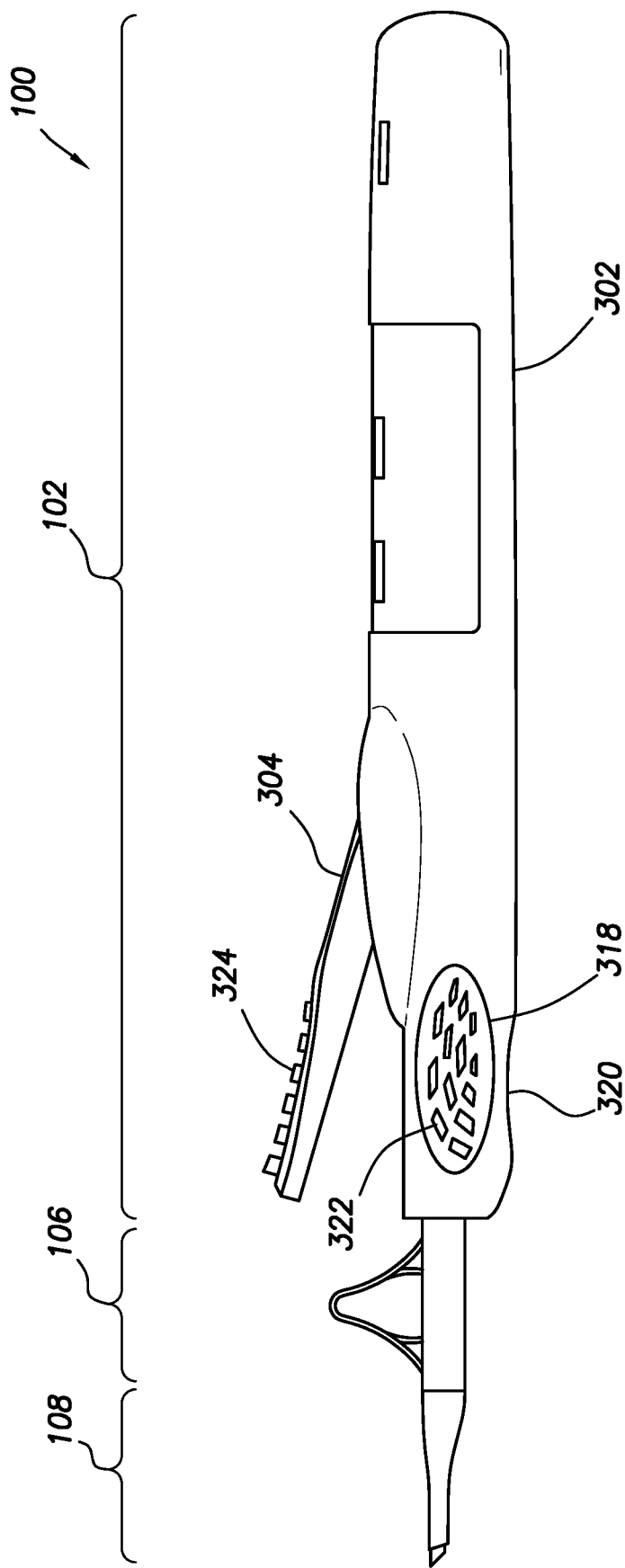
FIG. 5 illustrates a side view of the insertion tool of FIG. 3.

FIGS. 3-5 illustrate an example insertion tool 100 operable to deliver an IOL into the eye (e.g., IOL 110 in eye 200 shown on FIGS. 2A and 2B). As illustrated, the insertion tool 100 includes a drive system 102, a haptic optic management system 106, and a nozzle 108. The insertion tool 100 may also include a plunger, which may be similar to the plunger 104 shown in FIG. 1. In some instances. The plunger 104 may be actuated to advance an IOL, e.g., which may be similar to the IOL 110 shown in FIG. 1, within the insertion tool 100 and, in some cases, dispense the IOL 110 from the insertion tool 100.

Referring to FIG. 3, the drive system 102 includes a body 302 and a lever 304 that may be pivotally coupled to the body 302. The nozzle 108 is coupled to a distal end 308 of the body 302. The HOMS 106 is disposed between the body 302 and the nozzle 108. In some instances, the nozzle 108 may be integrally connected to the body 302. In other instances, the nozzle 108 may be separate from the body 302 and may be coupled to the body 302 via an interlocking relationship. In some instances, the HOMS 106 and the nozzle 108 may be integrally formed. In other instances, the HOMS 106, the nozzle 108, and the body 302 may be integrally formed.

In some instances, the body 302 may have a slender, elongated shape. In some instances, the body 302 may have a first portion 310 and a second portion 312. In some instances, the second portion 312 may be at least partially disposed over the first portion 310. In the example shown, the second portion 312 includes a plurality of apertures 314. A plurality of tabs 316 formed on the first portion 310 are received into the apertures 314 to join the first portion 310 and the second portion 312. The tabs 316 may form an interlocking fit with the apertures 314. However, the construction of the body 302 of the example insertion tool 100 shown in FIGS. 3-5 is merely a non-limiting example. In some instances, the body 302 may be a single unitary piece. In some instances, the body 302 may include one or more cylindrical pieces. Moreover, the body 302 may be constructed in any desirable manner from any number of components.

With reference to FIGS. 3-5, the body 302 also includes reliefs 318, 319, and 320. The reliefs 318, 319, and 320 are shallow recesses formed in the body 302 to accommodate, for example, one or more fingers of a user. One or more of the reliefs 318, 319, and 320 may include a textured surface 322 that may provide a user with an improved grip of and control over the insertion tool 100. As shown in FIGS. 3 and 5, the relief 318 may include texture surface 322. However, the scope may not be so limited. Rather any, all, or none of the reliefs 318, 319, and 320 may include the textured surface 322. Similarly, the lever 304 may also include a textured surface 324. However, in some instances, the lever 304 may not include a textured surface.

Referring to FIG. 3, the nozzle 108 includes a distal tip 326 that defines an opening 328. The nozzle 108 also includes a flared portion or wound guard 330. The distal tip 326 may be adapted to be inserted into an incision formed in an eye, such as the incision 202 in eye 200 shown on FIGS. 2A and 2B, in order to deliver a folded IOL thereinto. The wound guard 330 may include an end surface 332 operable to contact an exterior surface in order to limit a depth to which the distal tip 326 penetrates the eye 200. In some embodiments, the wound guard 330 may be omitted.

In some embodiments, the insertion tool 100 may be preloaded. That is, the insertion tool 100 may include an IOL disposed therein when provided to an end user. In some instances, the IOL may be disposed within the insertion tool 100 in an unfolded state and ready to be delivered into a patient. Having the insertion tool 100 preloaded with an IOL reduces the number of steps a user must perform both before delivering the IOL into a patient. For example, a preloaded insertion tool obviates any steps a user would otherwise be required to perform in order to load the insertion tool with the IOL. With a reduced number of steps, error and risk associated with delivery of the IOL into a patient may be reduced. Further, an amount of time required to deliver the IOL may also be reduced. In some embodiments, the IOL may be preloaded into the haptic optic management system 106.

Figure 6:
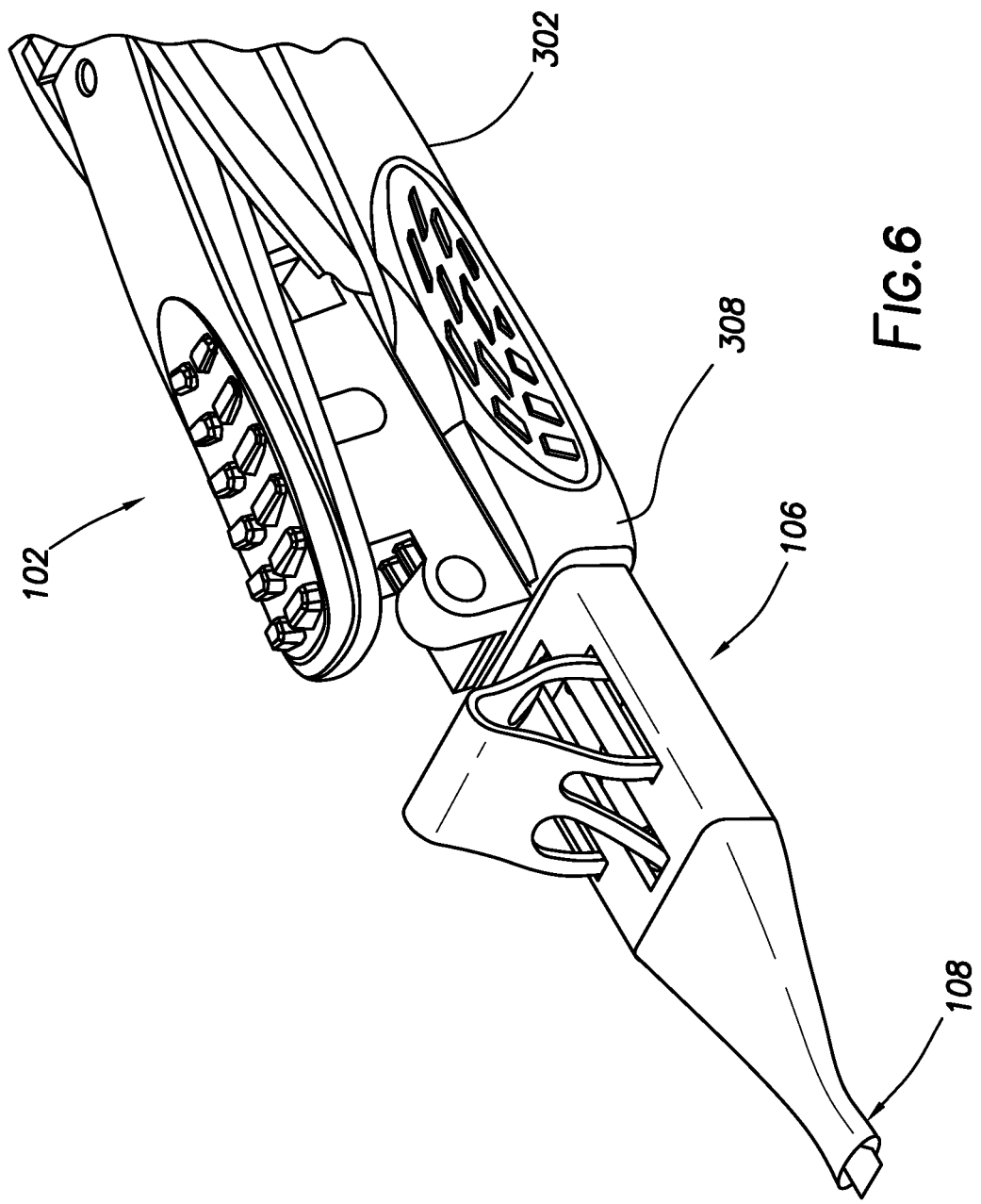
FIG. 6 is a detail view of a distal end of the insertion tool of FIG. 3.

FIG. 6 illustrates a close-up view of an example insertion tool 100 with a haptic optic management system 106. The HOMS 106 is operable to folds the IOL. For example, in some instances, the HOMS 106 may be operable to fold an IOL from an unstressed condition to a fully folded configuration, as shown in FIG. 1, for example. During folding, the HOMS 106 may tuck or fold the haptics 112 over the optic 114 of the IOL 110 as well as fold edges of the optic 114 over the tucked haptics 112, capturing the haptics 112 and thereby placing the IOL 110 into the folded configuration, as shown in FIG. 1, for example.

As shown in FIGS. 3-6, for example, the HOMS 106 is sized to commensurate with a size of the insertion tool 100. That is, the HOMS 106 has a compact size to avoid or limit an amount of obstruction to a surgeon's view while inserting an IOL into an eye. However, the scope of the disclosure is not so limited. Rather, in some instances, a size and/or shape of the haptic optic management system may be selected to be any desired size or shape. Further, while the HOMS 106 is shown disposed at the distal end of the insertion tool 100, the haptic optic management system 106 may be disposed anywhere within or along the insertion tool 100. In some embodiments, the HOMS 106 may be disposed between the nozzle 108 and the drive system 102.

In the illustrated example of FIGS. 3-6, the HOMS 106 is disposed between the distal end 308 of the body 302 and the nozzle 108. In some instances, the HOMS 106 may be removably coupled to the nozzle 108 and/or the drive system 102. For example, the HOMS 106 may be removably coupled to the body 302 with the use of fasteners or adhesives. In still other implementations, the HOMS 106 may couple to the body 302 by a snap-fit engagement or any other desired method of connection. Without limitation, example fasteners may include nuts and bolts, washers, screws, pins, sockets, rods and studs, hinges and/or any combination thereof.

Figure 7:
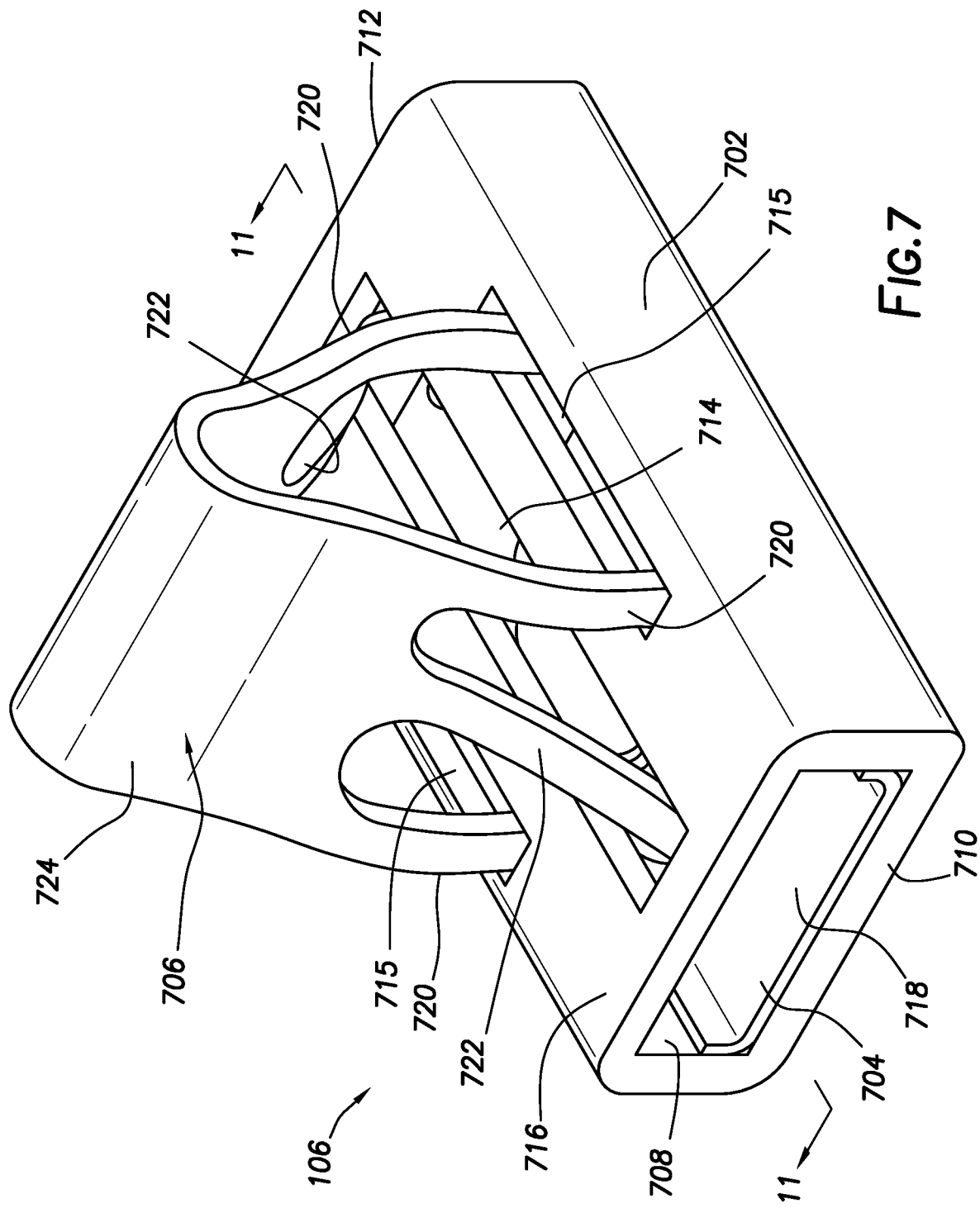
FIG. 7 illustrates an example haptic optic management system that includes a clip.

FIG. 7 illustrates an example haptic optic management system 106. In the illustrated example, the HOMS 106 includes a housing 702, a plate 704, and a clip 706. The housing 702 may be a protective covering for the IOL 110 (e.g., shown on FIG. 1) that is to be manipulated within the insertion tool 100. The housing 702 may be made from materials, such as, for example, metals, nonmetals, polymers, ceramics, and/or combinations thereof. The housing 702 may have any suitable size and/or shape for accommodating an IOL, such as the IOL 110 shown on FIG. 1. For example and without limitation, the housing 702 may be shaped such that all or a portion of the housing 702 may have a cross-sectional shape that is circular, elliptical, triangular, rectangular, square, hexagonal, and/or combinations thereof. In other embodiments, all or a portion of the housing 702 may have a rectangular cross-sectional shape. The housing 702 includes a through bore 708 that traverses the entire length from a first end 710 of the housing 702 to a second end 712 of the housing 702. The through bore 708 defines a path through which a plunger 104 advances to engage an IOL and 110 drive the IOL 110 through the HOMS 106, as shown on FIG. 1. In some implementations, the plunger 104 continues to drive the IOL 110 through the nozzle 108 of the insertion tool 100 and expel the IOL 110 from the insertion tool 100, as shown on FIG. 1. In the example shown in FIG. 8, the through bore 708 has a rectangular cross-section. However, the scope of the disclosure is not so limited. In other implementations, the through bore 708 may have a cross-sectional shape that is U-shaped, circular, oval, rectangular, square, triangular, polygonal, or any other cross-sectional shape.

Additionally, there may be one or more openings, shown on FIG. 7 as central slit 714 and pair of slits 715, disposed on one or more sides 716 of the housing 702. As illustrated, the central slit 714 and the pair of slits 715 are parallel and formed in the housing 702 in the same direction as the through bore 708. In addition, the pair of slits 715 are disposed on either side of the central slit 714. The central slit 714 and the pair of slits 715 may be disposed on any of the one or more sides 716 of the housing 702 and/or on a plurality of the one or more sides 716 of the housing 702. Without limitation, there may a single central slit 714 and two or more individual slits in each pair of slits 715. The central slit 714 and the pair of slits 715 provide access to the through bore 708 from the outside of the housing 702.

The plate 704 is disposed in the through bore 708. The plate 704 has a lens surface 718 upon which an IOL is disposed, such as the IOL 110 shown on FIG. 1. The plate 704 may roll the IOL 110 such that the IOL 110 folds upon itself. The plate 704 may be made from an elastic material, such as a shape memory material. Suitable materials may include, but are not limited to, nonmetals, polymers, ceramics, and/or combinations thereof. Without limitation, the plate 704 may be made from spring steel, nitinol, polyimide, silicone, coated metals, and/or the like. The plate 704 may have any suitable size and/or shape for holding the IOL 110. For example and without limitation, the plate 704 may be shaped such that all or a portion of the plate 704 may have a cross-sectional shape that is circular, elliptical, triangular, rectangular, square, hexagonal, and/or combinations thereof. In other embodiments, all or a portion of the plate 704 may have a rectangular cross-sectional shape for placement in the through bore 708.

In embodiments, the clip 706 is in removable engagement with the plate 704 within the housing 702. The clip 706 holds the plate 704 such that the lens surface 718 is flat within the through bore 708 of the housing 702. The clip 706 is referred to as being a "squid" as it includes a plurality of legs, shown on FIG. 7 as outer support legs 720 and inner legs 722. The clip 706 includes a clip body 724 from which the outer support legs 720 and the inner legs 722 extend. The clip body 724 couples the outer support legs 720 and the inner legs 722 in a hinge-like fashion so that flexible compression of the clip body 724 causes the outer support legs 720 and the inner legs 722 to compress closer together. As illustrated, the outer support legs 720 extend into the pair of slits 715 and the inner legs 722 extend into the central slit 714. In the housing 702, the outer support legs 720 engage the plate 704. The outer support legs 720 keep the plate 704 in a flat position. In some instances, the plate 704 is predisposed to roll or fold in upon itself. This may be due to the way the plate 704 was manufactured, and/or the plate 704 may have been conditioned to roll or fold in upon itself by an external force. By disposing the outer support legs 720 within the housing 702, the outer support legs 720 engage the plate 704 and prevent the plate 704 from moving. The clip 706 may be made from materials, such as, for example, metals, nonmetals, polymers, ceramics, and/or combinations thereof. Without limitation, the clip 706 may be made from a medical grade plastic such as polypropylene, polycarbonate, and/or the like. The clip 706 may have any size and/or shape. For example and without limitation, the clip 706 may be shaped such that all or a portion of the clip 706 may have a cross-sectional shape that is circular, elliptical, triangular, rectangular, square, hexagonal, and/or combinations thereof.

Figure 8:
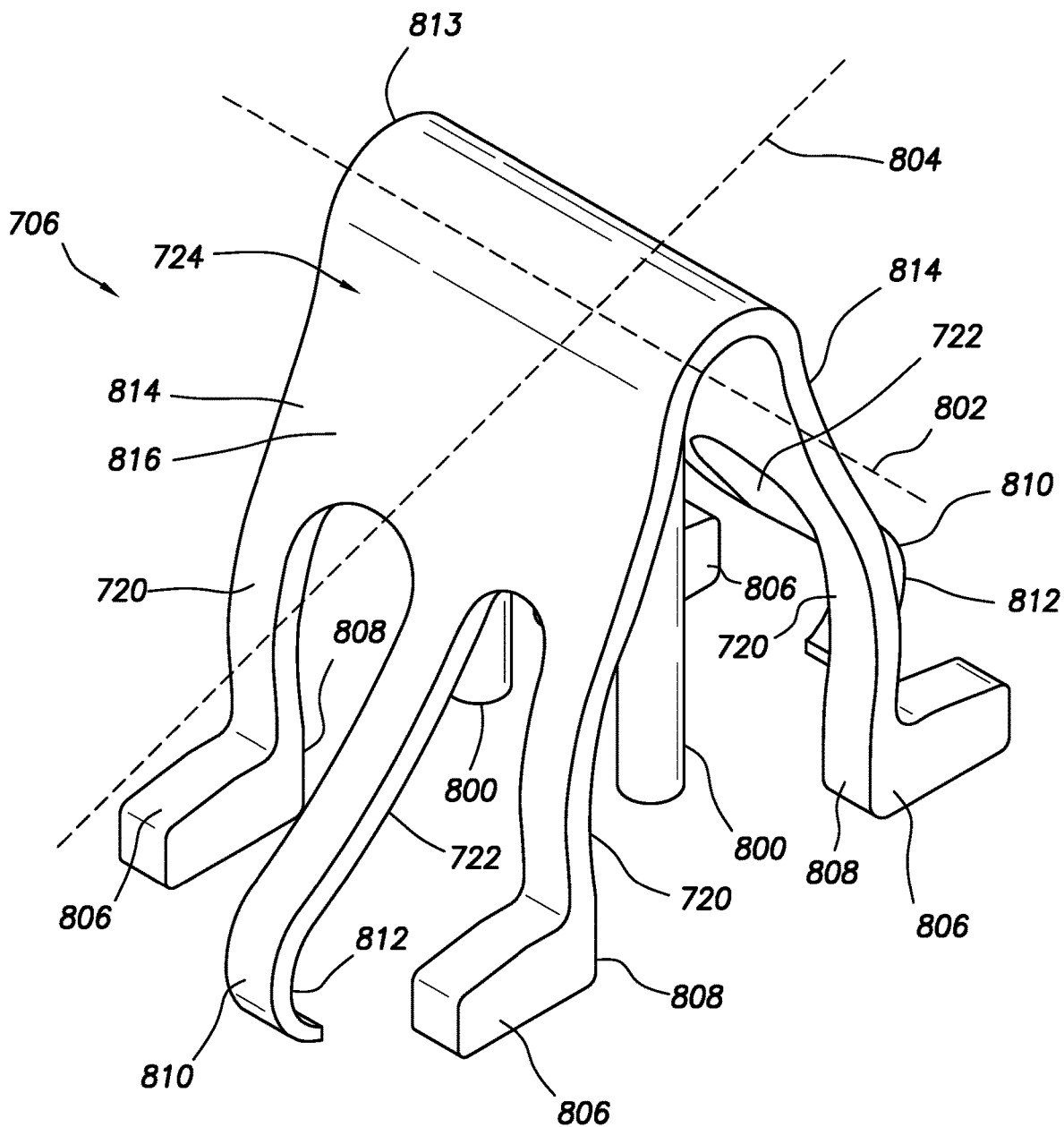
FIG. 8 illustrates a clip of the example haptic optic management system of FIG. 7.

FIG. 8 is a perspective view of the clip 706. As illustrated, the clip 706 includes the outer support legs 720, the inner legs 722, and the clip body 724. As illustrated, the outer support legs 720 extend from the clip body 724. In some embodiments, there may be four outer support legs 720. However, embodiments may include more or less than four of the outer support legs 720. In some examples, there are two outer support legs 720 disposed on one side of the clip 706 and two outer support legs 720 disposed on another side of the clip 706, wherein each outer support leg 720 is reflected from the position of another outer support leg 720 across an X-axis 802 of the clip 706 and a Y-axis 804 of the clip 706. The outer support legs 720 provide structural support and stability to the clip 706. A foot 806 may be coupled to each of the outer support legs 720. As illustrated, the foot 806 may be coupled to a distal end 808 of each of the outer support legs 720. The foot 806 may be integrally connected to each of the outer support legs 720. In other instances, the foot 806 may be separate from the outer support leg 720 and may be coupled to the outer support leg 720 via an interlocking relationship. In some instances, the outer support leg 720 and foot 806 may be integrally formed.

Additionally, the clip 706 includes a plurality of the inner legs 722. As shown, there are two inner legs 722. However, the clip 706 may include more or less than two inner legs 722 depending, for example, on the particular application. Each of the inner legs 722 are disposed between two of the outer support legs 720. In some embodiments, each of the inner legs 722 is in the same relative position reflected across the X-axis 802 of the clip 706. The inner legs 722 each include a curved portion 810 at a distal end 812 of each of the inner legs 722.

In some instances, the clip 706 includes a plurality of center posts 800. As shown, there are two of the center posts 800. However, the clip 706 may include more or less than two center posts 800 depending, for example, on the particular application. In some embodiments, each center post 800 is in the same relative position reflected across the Y-axis 804 of the clip 706. The center posts 800 may have any size and/or shape. For example and without limitation, the center posts 800 may be shaped such that all or a portion of the center posts 800 may have a cross-sectional shape that is circular, elliptical, triangular, rectangular, square, hexagonal, and/or combinations thereof. In other embodiments, all or a portion of the center posts 800 may have a circular cross-sectional shape. The center posts 800 align the clip 706 with the pair of slits 715 (e.g., referring to FIG. 7) of the housing 702. The center posts 800 provide additional structural support for the clip 706. The center posts 800 also serve to hold the IOL 110 (e.g., referring to FIG. 1) in a stationary position prior to actuation of the HOMS 106 (e.g., referring to FIG. 1).

The clip body 724 of the clip 706 may have any size and/or shape. For example and without limitation, the clip body 724 may be shaped such that all or a portion of the clip body 724 may have a cross-sectional shape that is circular, elliptical, triangular, rectangular, square, hexagonal, and/or combinations thereof. In other embodiments, all or a portion of the clip body 724 may by U-shaped. However, embodiments of the clip body 724 may also be c-shaped, v-shaped, or otherwise formed for the clip body 724 to couple the outer support legs 720 and the inner legs 722 in a hinge-like fashion such that compression of the clip body 724 causes the outer support legs 720 and the inner legs 722 to compress closer to one another. The clip body 724 may be symmetric or asymmetric across the X-axis 802 and/or the Y-axis 804. In some instances, the clip body 724 provides one or more gripping surfaces 816 for an operator. As illustrated, the clip body 724 includes a spring portion 813 and opposing gripping portions 814 that include the gripping surfaces 816. The opposing gripping portions 814 extend from the spring portion 813. As illustrated, the center posts 800 extend from the spring portion 813. The outer support legs 720 and the inner legs 722 extend from the gripping portions 814. In operation, the clip body 724 is actuated by a force, such as a compression force. The force may compress the clip body 724, for example, by squeezing the gripping portions 814 together, which causes outer support legs 720 and/or the inner legs 722 to translate in the same path of motion as the direction of the force acting on the clip body 724. In examples, the clip body 724 biases the outer support legs 720 and the inner legs 722 such that when the force is removed, the outer support legs 720 and the inner legs 722 return to their original position.

Figure 9:
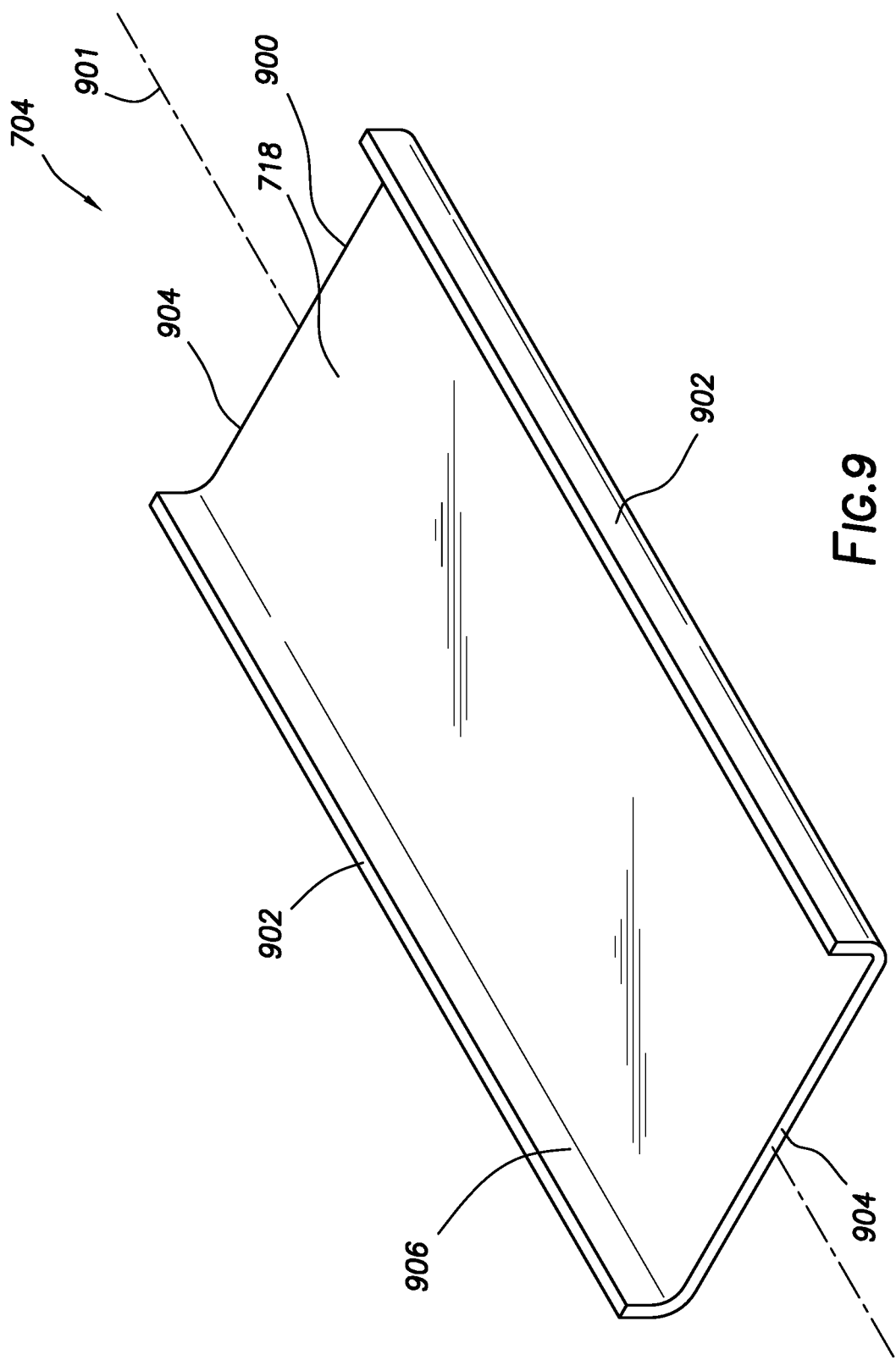
FIG. 9 illustrates a plate in a first position of the example haptic optic management system of FIG. 7.
Figure 10:
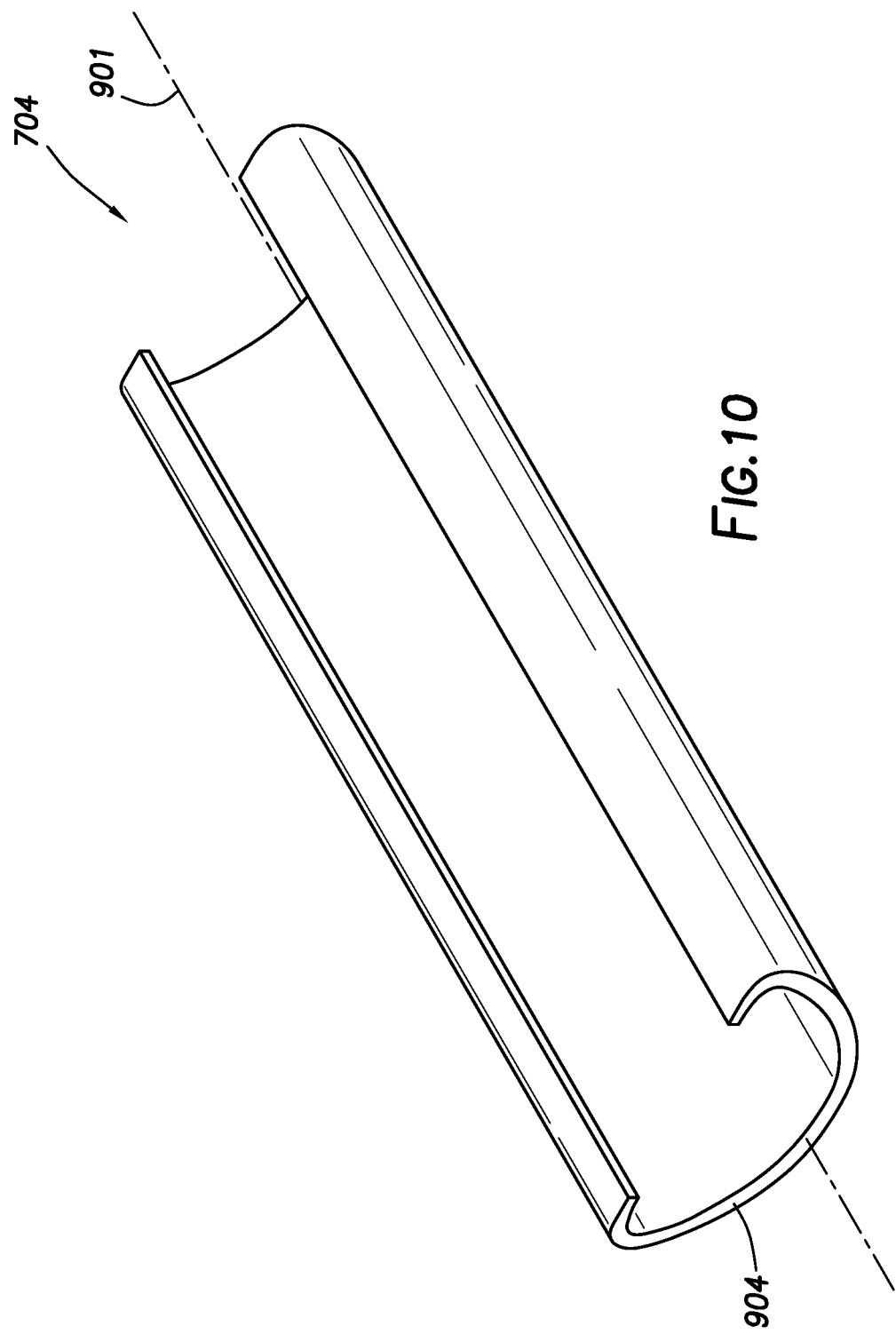
FIG. 10 illustrates a plate in a second position of the example haptic optic management system of FIG. 7.

FIG. 9 is a perspective view of the plate 704. As illustrated, the plate 704 includes a base 900 and sidewalls 902. The base 900 has a longitudinal axis 901. The base 900 includes a lens surface 718. The base 900 also includes ends 904 and lateral sides 906 that extend between the ends 904. The sidewalls 902 extend upwards from the lateral sides 906. As illustrated, the sidewalls 902 extend the entire length between the ends 904, but embodiments may include extended sidewalls 902 for a portion of the length between the ends 904. As previously described, the plate 704 may be predisposed to roll or fold in upon itself. This may be due to the way the plate 704 was manufactured, and/or the plate 704 may have been conditioned to roll or fold in upon itself by an external force. FIG. 9 illustrates the plate 704 in a first position. As illustrated, the base 900 is generally flat in the first position. A force may be applied to the base 900 to maintain the first position. The plate 704 may have a second position that is the unstressed or pre-deformed position of the plate 704. The plate 704 may be elastic so that when the force is removed the plate returns to the second position. When the force is removed, the plate 704 rolls or folds in upon itself into a second position, as illustrated on FIG. 10. In the illustrated embodiment, the plate 704 rolls about the longitudinal axis 901 of the base 900.

Figure 11:
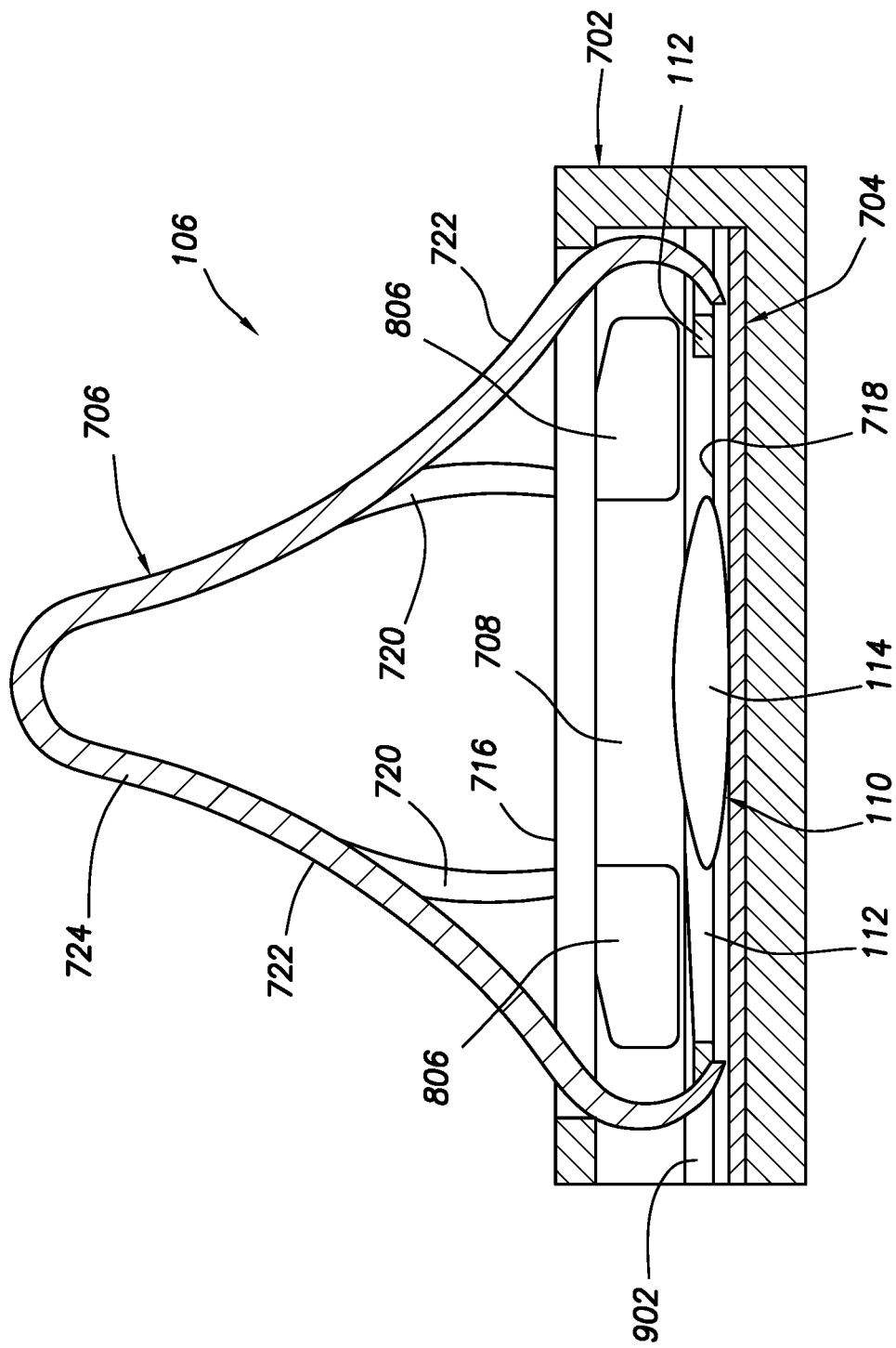
FIG. 11 illustrates a cross-sectional view of the example haptic optic management system of FIG. 7.

FIG. 11 illustrates a cross-sectional view of the haptic optic management system 106 of FIG. 7 taken along line 11-11. As illustrated, the HOMS 106 includes a housing 702, a plate 704, and a clip 706. In examples, IOL 110 is disposed in the through bore 708 of the housing 702. As previously discussed, the IOL 110 may include the optic 114 and the haptics 112. The IOL 110 is disposed on the lens surface 718 of the plate 704. The IOL 110 may be in an unfolded state with the haptics 112 extending away from the optic 114. In some instances, the plate 704 may be predisposed to roll or fold in upon itself by an external force. The clip 706 is positioned to apply a force to the plate 704 preventing the plate 704 from rolling or otherwise folding in upon itself. As illustrated, the clip 706 includes the outer support legs 720 and the inner legs 722 that extend from the clip body 724. The outer support legs 720 extend into the pair of slits 715 (e.g., shown on FIG. 7) and the inner legs 722 extend into the central slit 714 (e.g., shown on FIG. 7) into the through bore 708. The feet 806 are coupled to each of the outer support legs 720. The feet 806 engage the plate 704 holding it in the first position (e.g., as best seen on FIG. 9). In some embodiments, the feet 806 engage the lens surface 718. In other instances, the feet 806 engage the sidewalls 902 of the plate 704.

Operation of the haptic optic management system 106 will now be described in more details. Referring to FIG. 11, the HOMS 106 may be pre-loaded with the IOL 110. As illustrated, the IOL 110 is disposed on the plate 704 in the housing 702. An operator actuates the clip 706, for example, by applying a force on the clip body 724 of the clip 706. The force compresses the clip body 724 also causing the opposing outer support legs 720 and the opposing inner legs 722 to move inward, closer together. As they move inward, the inner legs 722 come into contact with the haptics 112 of the IOL 110. The inner legs 722 move the haptics 112 over and on top of the optic 114. While the clip 706 is compressed, an operator can remove the clip 706 from the haptic optic management system 106. As the clip 706 is removed, the force applied to the plate 704 by the clip 706 (e.g., by way of the feet 806) is removed. Without this force, the plate 704 rolls, or at least partially rolls, in upon itself into the second position (as best seen on FIG. 10) as there is no longer a force and/or object preventing the plate 704 from moving. As the plate 704 rolls, the IOL 110 disposed on the lens surface 718 of the plate 704 rolls in upon itself as illustrated on FIG. 12.

In some embodiments, a haptic management system is configured without a plate and the clip 706 folds the haptics over and on top of an IOL. Also, in some cases, the IOL involves a base comprising a ring and haptics extending from the ring. In these cases, an IOL base can be inserted into an eye in a first surgical step and a separate optic can be inserted and coupled with the base at a second surgical step. Furthermore, the optic can be decoupled from the base and a further optic can be inserted and coupled to the already installed base at a subsequent surgical step. In these cases, for example, the haptic management system can be employed without a plate since the optic is not present and, therefore, would not need to be folded.

Figure 12:
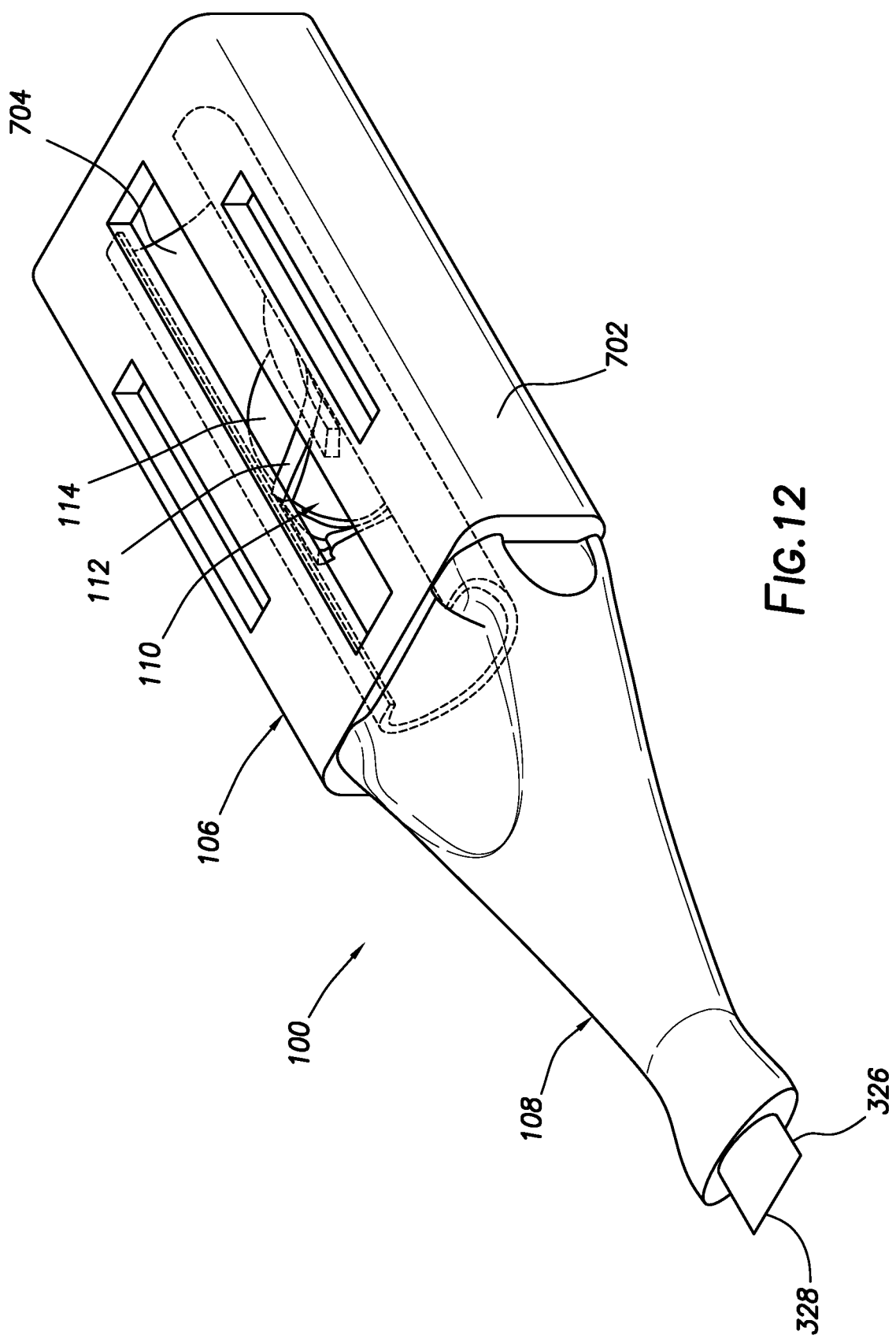
FIG. 12 illustrates an end of an insertion tool with the example haptic optic management system of FIG. 7.

In the illustrated embodiment of FIG. 12, the plate 704 is rolling in upon itself causing the IOL 110 to also roll in upon itself. As illustrated, the haptics 112 of the IOL 110 are disposed on the optic 114. After rolling the IOL 110 into a folded position, (e.g., folded configuration 116 shown on FIG. 1) the IOL 110 is dispensed from the insertion tool 100. By way of example, a drive system (e.g. drive system 102 shown FIG. 1) actuates to cause the IOL 110 to travel out of the haptic optic management system 106, through the nozzle 108, exiting out of the opening 328 at the distal tip 326 of the nozzle 108. Accordingly, the haptic optic management system 106 as described herein is used to prepare the IOL 110 for insertion into an eye, such as the eye 200 shown on FIGS. 2A and 2B.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A haptic optic management system, comprising:
    a housing, wherein:
        the housing comprises openings in a side of the housing,
        the openings comprise a central slit and a pair of slits, and
        the central slit is disposed between the pair of slits;
    a plate, wherein:
        the plate is disposed within the housing; and
    a clip that engages the plate in the housing, wherein:
        the clip extends through the openings into a through bore in the housing,
        the clip comprises a clip body and a plurality of legs that extend from the clip body into the housing,
        the plurality of legs comprises outer support legs that extend through the pair of slits in the housing to hold the plate in position and inner legs that extend through the central slit, and
        at least a portion of the plurality of legs are configured to compress closer together when an external force is applied to the clip body.

2. The haptic optic management system of claim 1, wherein the through bore traverses a length of the housing from a first end of the housing to a second end of the housing, wherein the plate is disposed in the through bore.

3. The haptic optic management system of claim 1, wherein the plate is elastic, and wherein the clip engages the plate to prevent the plate from returning to an original position.

4. The haptic optic management system of claim 1, wherein the plate comprises a material selected from the group consisting of spring steel, nitinol, polyimide, silicone, coated metals, and combinations thereof.

5. The haptic optic management system of claim 1, wherein an intraocular lens is disposed on a lens surface of the plate, wherein the intraocular lens comprises an optic and haptics that extend from a periphery of the optic.

6. A haptic optic management system, comprising:
    a housing;
    a plate, wherein:
        the plate is disposed within the housing; and
    a clip that engages the plate in the housing, wherein:
        the clip comprises a clip body and a plurality of legs that extend from the clip body into the housing,
        the clip body comprises a spring portion and opposing gripping portions that extend from the spring portion,
        the clip further comprises a center post that extends from the clip body,
        the center post aligns the clip within a pair of slits of the housing, and
        at least a portion of the plurality of legs are configured to compress closer together when an external force is applied to the clip body.

7. The haptic optic management system of claim 6, wherein the housing comprises a through bore traversing a length of the housing from a first end of the housing to a second end of the housing, wherein the plate is disposed in the through bore.

8. The haptic optic management system of claim 6, wherein the plate is elastic, and wherein the clip engages the plate to prevent the plate from returning to an original position.

9. The haptic optic management system of claim 6, wherein the plate comprises a material selected from the group consisting of spring steel, nitinol, polyimide, silicone, coated metals, and combinations thereof.

10. The haptic optic management system of claim 6, wherein an intraocular lens is disposed on a lens surface of the plate, wherein the intraocular lens comprises an optic and haptics that extend from a periphery of the optic.

11. An insertion tool, comprising:
    a drive system, wherein:
        the drive system comprises a body;
    a plunger disposed in the drive system;
    a nozzle; and
    a haptic optic management system positioned between the nozzle and the drive system for receiving a distal tip of the plunger, wherein the haptic optic management system comprises:
        a housing, wherein:
            the housing comprises a through bore traversing a length of the housing from a first end of the housing to a second end of the housing,
            the housing further comprises openings in a side of the housing,
            the openings comprise a central slit and a pair of slits, and the central slit is disposed between the pair of the slits;
a plate, wherein:
the plate is disposed in the housing, and
the plate is disposed in the through bore; and
a clip that engages the plate in the housing, wherein:
the clip extends through the openings into the through bore,
the clip comprises a clip body and a plurality of legs that extend from the clip body into the housing,
the plurality of legs comprises outer support legs extending through the pair of slits that hold the plate in position and inner legs extending through the central slit, and
at least a portion of the plurality of legs are configured to compress closer together when an external force is applied to the clip body.

12. The insertion tool of claim 11, wherein the haptic optic management system comprises an intraocular lens disposed on a lens surface of the plate, wherein the intraocular lens comprises an optic and haptics that extend from a periphery of the optic.

13. The insertion tool of claim 11, wherein the plunger is operable to engage an intraocular lens disposable in the haptic optic management system when the drive system is actuated to dispense the intraocular lens from the nozzle.

14. The insertion tool of claim 11, wherein the drive system comprises one of a lever and a pneumatic system, a mechanical system, and an electromechanical system.

15. The insertion tool of claim 11, wherein the plate is elastic, and wherein the clip engages the plate to prevent the plate from returning to an original position.

16. The insertion tool of claim 11, wherein the plate comprises a material selected from the group consisting of spring steel, nitinol, polyimide, silicone, coated metals, and combinations thereof.

17. A method of delivering an intraocular lens, comprising:
applying an external force upon a clip to compress the clip in a housing, wherein the housing contains the intraocular lens, wherein the intraocular lens comprises an optic and haptics that extend from a periphery of the optic;
engaging the haptics with the clip as the clip is compressed to cause the haptics to fold onto the intraocular lens;
moving the clip away from the intraocular lens to release a force applied to a plate holding the intraocular lens to cause the plate and the intraocular lens to roll; and
actuating a drive system to dispense the intraocular lens through a nozzle and into an eye, and
wherein the clip comprises a plurality of legs that extend into the housing, and wherein the applying the external force causes at least a portion of the legs to compress closer together.

18. The method of claim 17, wherein the plurality of legs comprise inner legs, wherein the inner legs engage the haptics to cause the haptics to fold over on top of the intraocular lens.

19. The method of claim 17, wherein the plurality of legs comprise outer support legs, wherein moving the clip away from the intraocular lens causes feet of the outer support legs to release from engagement with the plate such that the plate rolls upon itself.

20. The method of claim 17, wherein actuating the drive system causes a plunger to displace the intraocular lens out of the housing through the nozzle.

* * * * *